(12) United States Patent
Büttner et al.

(10) Patent No.: US 7,494,275 B2
(45) Date of Patent: Feb. 24, 2009

(54) X-RAY COMPUTED TOMOGRAPHY APPARATUS WITH A ROTOR FORMED OF COMPOSITE MATERIAL

(75) Inventors: Thorsten Büttner, Kirchehrenbach (DE); Tobias Gnutzmann, Nürnberg (DE); Uli Holzermer, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 184 days.

(21) Appl. No.: 11/523,476

(22) Filed: Sep. 19, 2006

(65) Prior Publication Data
US 2007/0064863 A1 Mar. 22, 2007

(30) Foreign Application Priority Data
Sep. 19, 2005 (DE) .................. 10 2005 044 655

(51) Int. Cl.
*H05G 1/02* (2006.01)
(52) U.S. Cl. .......................... 378/193; 378/4

(58) Field of Classification Search .............. 378/4, 378/15, 193, 197, 205; 439/13
See application file for complete search history.

(56) References Cited

U.S. PATENT DOCUMENTS

| 5,031,198 | A |   | 7/1991 | Deucher et al. |
| 5,305,520 | A | * | 4/1994 | Doorbar et al. .......... 29/889.21 |
| 5,840,390 | A | * | 11/1998 | Fujiwara ..................... 428/37 |
| 6,337,894 | B1 |   | 1/2002 | Tybinkowski et al. |
| 2008/0025844 | A1 | * | 1/2008 | Bayer et al. ................ 416/221 |

FOREIGN PATENT DOCUMENTS

WO   WO 2005/056983 A1 * 6/2005

* cited by examiner

*Primary Examiner*—Jurie Yun
(74) *Attorney, Agent, or Firm*—Schiff Hardin LLP

(57) ABSTRACT

An x-ray computed tomography apparatus has a rotor on which are mounted at least one x-ray source and one detector. To avoid unwanted deformations of the rotor at high rotation speeds, the rotor is produced at least in segments from a fiber-reinforced composite material with a metal matrix.

10 Claims, 1 Drawing Sheet

X-RAY COMPUTED TOMOGRAPHY APPARATUS WITH A ROTOR FORMED OF COMPOSITE MATERIAL

BACKGROUND OF THE INVENTION

1. Field of the Invention

The present invention concerns an x-ray computed tomography apparatus.

2. Description of the Prior Art

X-ray computed tomography apparatuses are generally known that have at least one x-ray source and one detector mounted on a rotatable part or rotor of a gantry. Such a rotor with the components mounted thereon weighs up to 1.4 t. It is rotated with rotation speeds up to 180 revolutions/minute. Significant centrifugal forces thereby arise. As a result, a deformation of the rotor can occur upon rotation. This is in turn detrimental to the precise alignment of the x-ray beam emitted by the x-ray source onto the oppositely-situated detector, and thus is also detrimental to the quality of the generated x-ray images.

In order to counteract this disadvantage, according to the prior art the geometry of the rotor has been optimized such that the centers of gravity of nearly all components mounted on the rotor lie in a center of gravity plane. Ribs that are connected with a circumferential (peripheral) outer wall of the rotor are also provided on the rotor base to increase the rigidity of the rotor. Computational simulations have shown, however, that unwanted deformations occur again given an increase of the rotation speeds.

SUMMARY OF THE INVENTION

An object of the invention is to overcome the disadvantages according to the prior art. An x-ray computed tomography apparatus is provided that can be operated without quality loss given image generation with high rotor rotation speeds.

This object is achieved in accordance with the invention wherein the rotor is produced at least in segments from a fiber-reinforced composite material with a metal matrix. The rigidity of the rotor can be significantly improved with such material in a simple manner. The rotor can be rotated at higher rotation speeds without unwanted deformation occurring. A good image quality can be achieved with this rotor even at high rotation speeds.

In an embodiment of the invention, the composite material is surrounded at least in segments with a cladding of aluminum. This enables the production of a particularly smooth surface. This safely and reliably prevents anomalies that may possibly form in the composite material from detaching from the rotor. Apart from this, a particularly exact balancing of the rotor can be achieved on the aluminum cladding, for example by bores made therein.

In a further embodiment the fibers are produced of $Al_2O_3$. Such fibers are particularly light and give the composite material an excellent improvement in the rigidity. Naturally, instead of fibers produced from $Al_2O_3$ fibers produced from other suitable materials (for example SiC, AlN and the like) can also be used.

In a further embodiment a metal matrix is formed from aluminum or an aluminum alloy. By the use of such light metal the weight of the rotor, and thus the arising centrifugal forces, can be kept low. Naturally it is possible to also use other light metals (for example magnesium or the like) instead of aluminum for production of the rotor.

The rotor has a rotor base and a circumferential outer rotor wall at its periphery. The outer rotor wall allows components that may detach from the rotor floor upon a breakage of fastening elements to be caught, and thus an endangerment of persons located in proximity to the x-ray computed tomography apparatus can be avoided.

Furthermore, the rotor floor can be provided with reinforcing structures such as ribs and/or webs. The ribs and/or webs can be connected with the outer rotor wall. The rigidity of the rotor thus can be further improved.

According to a further embodiment, fastening segments fashioned without the use of fibers are provided on the rotor. Such fastening segments serve for the attachment of components on the rotor. They are typically provided with internal threadings for acceptance of threaded bolts corresponding thereto.

According to a further embodiment, the fibers in the region of the rotor floor are aligned essentially parallel to the top and bottom of the rotor base. The fibers in the region of the ribs and/or webs can likewise be aligned essentially parallel to the direction of the longitudinal extension of the ribs and/or webs. The fibers in the region of the outer rotor wall are appropriately aligned essentially tangentially. Due to this alignment of the fibers, the rigidity of the rotor can be further increased in the direction of the maximum stresses occurring in operation.

DESCRIPTION OF THE PREFERRED EMBODIMENTS

Figure 1:
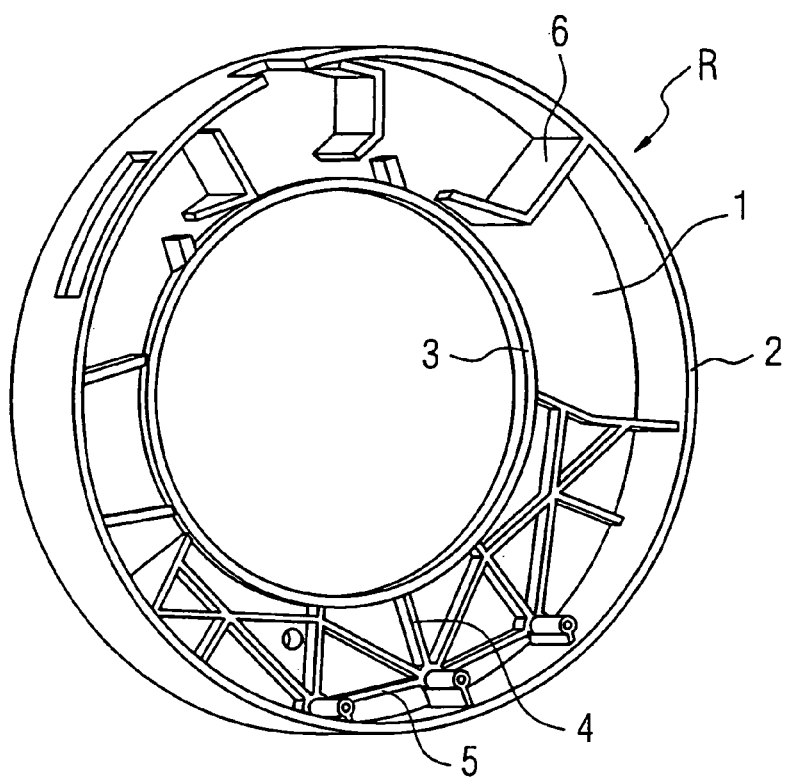
FIG. 1 is a perspective view of a rotor in accordance with the invention.

FIG. 1 shows a perspective view of a rotor generally designated R. The rotor R has a rotor base 1 which is fashioned in the form of an annular disc. The rotor base 1 is surrounded at its outer periphery by a circumferential outer rotor wall 2. An inner rotor wall 3 rises only slightly above the level of the rotor base 1 in comparison to the outer rotor wall 2. The rotor base 1 has a number of ribs 4 which run radially from the inner rotor wall 3 to the outer rotor wall 2. In addition to these, further ribs 5 running transversally and walls 6 running essentially radially are provided.

Figure 2:
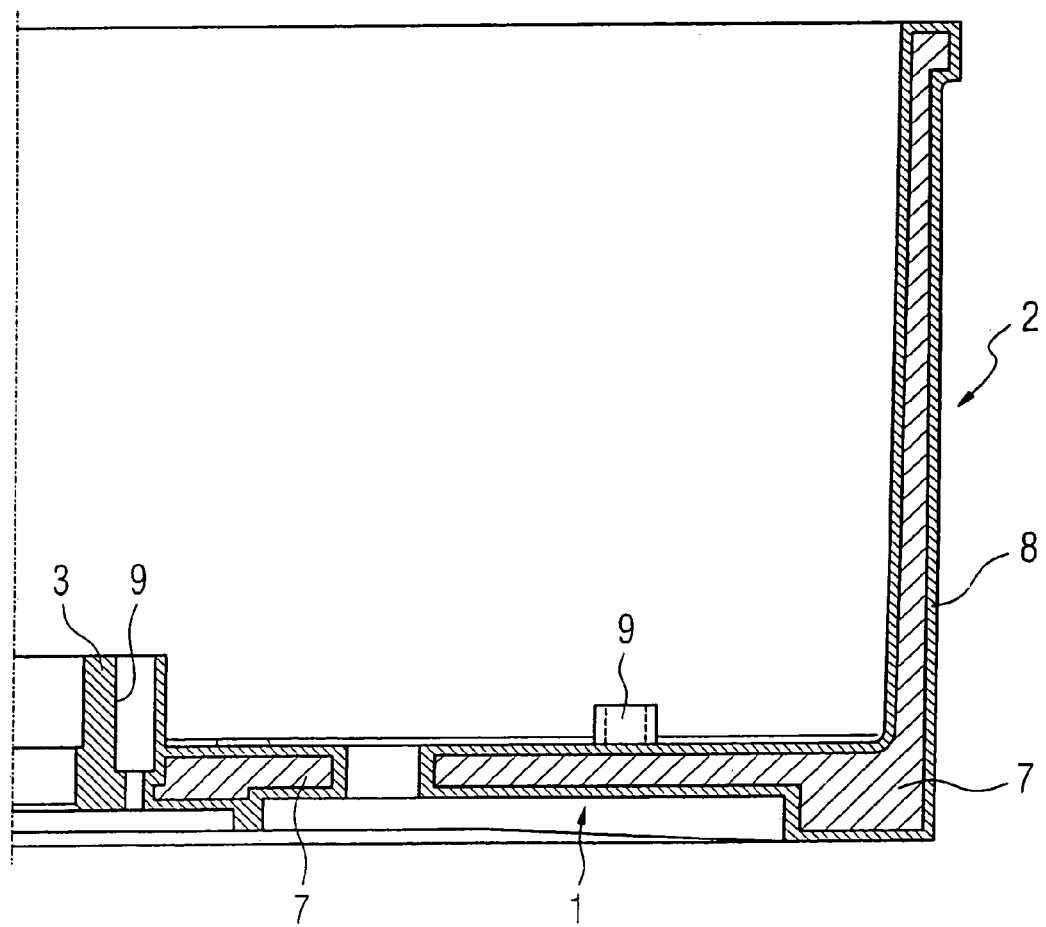
FIG. 2 is a partial cross-sectional view through the rotor according to FIG. 1.

FIG. 2 shows a partial cross-section through a segment of the rotor R extending from the outer rotor wall 2 to the inner rotor wall 3. As is apparent from FIG. 2, the rotor R has one or more composite material element(s) 7 produced from a composite material, the composite material element(s) 7 each being surrounded with a cladding 8 produced from a light metal, advantageously from aluminum or an aluminum alloy. In addition, segments of the rotor R (here the inner rotor wall 3) are exclusively formed of light metal. The composite material-free segments normally have attachment structures 9, for example threaded bores and the like.

To produce the composite material elements 7 a powdered metal can be mixed with fibers (for example fibers produced from $Al_2O_3$, SiC or the like) and subsequently be pressed into formed parts (molds) and then sintered. Such composite material elements 7 then can be placed into a conventional casting mold and the casing 8 can subsequently be produced recasting with a light metal, for example an aluminum alloy.

Naturally it is also possible to inlay pressed parts produced only from fibers into a casting form and to subsequently infuse this with a light metal.

The composite material elements 7 can be produced such that a preferential direction of the fibers runs parallel to the direction of the maximum tensile load given operation of the rotor R.

The rotor R can also have a composite material element 7 produced in a one-piece design, the composite material element 7 having both the rotor base 1 and the outer rotor wall 2. The inner rotor wall 3 can be additionally cast together with the cladding 8.

The composite material elements 7 produced from composite material appropriately exhibit an modulus of elasticity in the range from 320 to 420 Gpa (preferably 380 to 400 Gpa) and a density in the range from 3.2 to 4.0 $G/cm^3$ (preferably 3.4 to 3.95 $G/cm^3$). The shear modulus G normally lies between 42 and 58 Gpa, preferably between 45 and 57 Gpa.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an x-ray computed tomography apparatus having a rotatably mounted rotor with an x-ray source and a radiation detector mounted thereon, the improvement comprising said rotor comprising segments with at least some of said segments being comprised of a fiber-reinforced composite material with a metal matrix, and an aluminum cladding surrounding at least some of said segments that are comprised of fiber-reinforced composite material with a metal matrix.

2. The improvement of claim 1 wherein said fiber reinforced composite material with a metal matrix contains $Al_2O_3$ fibers.

3. The improvement of claim 1 wherein said metal matrix is comprised of metal selected from the group consisting of aluminum and aluminum alloys.

4. The improvement of claim 1 wherein said rotor has a rotor base with a periphery, and a circumferential outer rotor wall at said periphery.

5. The improvement of claim 4 wherein said rotor base has reinforcing structures attached thereto, selected from the group consisting of ribs and webs.

6. The improvement of claim 5 wherein said reinforcing structures are connected to said circumferential outer rotor wall.

7. The improvement of claim 1 wherein at least one of said x-ray source and said radiation detector is attached to the rotor at a fastening segment, and wherein said fastening segment is free of fibers.

8. The improvement of claim 1 wherein said rotor has a rotor base with a top and a bottom, and wherein said rotor base is comprised of said fiber-reinforced composite material with a metal matrix having fibers therein oriented substantially parallel to said top and bottom of said rotor base.

9. The improvement of claim 8 comprising a plurality of reinforcing structures attached to said rotor base and each having a longitudinal extent, said reinforcing structures being comprised of said fiber-reinforced composite material with a metal matrix having fibers therein oriented substantially parallel to said longitudinal extent.

10. The improvement of claim 8 wherein said rotor base has a periphery with a circumferential outer rotor wall located at said periphery, said circumferential outer rotor wall being comprised of said fiber-reinforced composite material with a metal matrix having fibers therein oriented substantially tangentially to said circumferential outer rotor wall.

\* \* \* \* \*